(12) United States Patent
Duchamp

(10) Patent No.: US 6,837,870 B2
(45) Date of Patent: Jan. 4, 2005

(54) CATHETER HAVING A MULTILAYERED SHAFT SECTION WITH A REINFORCING MANDREL

(75) Inventor: Jacky G. Duchamp, Campbell, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 304 days.

(21) Appl. No.: 10/202,343

(22) Filed: Jul. 23, 2002

(65) Prior Publication Data

US 2004/0019324 A1 Jan. 29, 2004

(51) Int. Cl.$^7$ .............................................. A61M 29/00
(52) U.S. Cl. ............................. 604/96.01; 604/103.04; 623/1.11
(58) Field of Search ...................... 604/96.01, 103.04, 604/103.09, 523–525, 528; 606/192, 194; 623/1.11

(56) References Cited

U.S. PATENT DOCUMENTS

| | | | |
|---|---|---|---|
| 4,748,982 A | 6/1988 | Horzewski et al. | |
| 4,752,129 A | 6/1988 | Izumi et al. | |
| 4,775,371 A | 10/1988 | Mueller, Jr. | |
| 5,176,637 A | * 1/1993 | Sagae | 604/103.14 |
| 5,180,367 A | 1/1993 | Kontos et al. | |
| 5,242,396 A | 9/1993 | Evard | |
| 5,334,147 A | * 8/1994 | Johnson | 604/103.04 |
| 5,364,376 A | * 11/1994 | Horzewski et al. | 604/528 |
| 5,387,193 A | 2/1995 | Miraki | |
| 5,389,087 A | 2/1995 | Miraki | |
| 5,413,559 A | * 5/1995 | Sirhan et al. | 604/103.04 |
| 5,425,711 A | 6/1995 | Ressemanne et al. | |
| 5,456,680 A | 10/1995 | Taylor et al. | |
| 5,458,613 A | 10/1995 | Gharibadeh et al. | |
| 5,489,271 A | 2/1996 | Andersen | |
| 5,496,346 A | 3/1996 | Horzewski et al. | |
| 5,507,768 A | 4/1996 | Lau et al. | |
| 5,531,690 A | 7/1996 | Solar | |
| 5,545,134 A | 8/1996 | Hilaire et al. | |
| 5,545,138 A | 8/1996 | Fugoso et al. | |
| 5,549,552 A | * 8/1996 | Peters et al. | 604/103.1 |
| 5,607,394 A | 3/1997 | Andersen et al. | |
| 5,626,600 A | 5/1997 | Horzewski et al. | |
| 5,634,902 A | * 6/1997 | Johnson et al. | 604/96.01 |
| 5,755,685 A | 5/1998 | Andersen | |
| 5,782,740 A | 7/1998 | Schneiderman | |
| 5,795,325 A | 8/1998 | Valley et al. | |
| 5,810,867 A | 9/1998 | Zarbatany et al. | |
| 5,823,995 A | 10/1998 | Fitzmaurice et al. | |
| 5,868,706 A | 2/1999 | Cox | |
| 5,882,336 A | 3/1999 | Janacek | |
| 5,897,536 A | 4/1999 | Nap et al. | |
| 5,931,812 A | 8/1999 | Andersen et al. | |
| 6,152,909 A | * 11/2000 | Bagaoisan et al. | 604/523 |
| 6,193,686 B1 | * 2/2001 | Estrada et al. | 604/103.09 |
| 6,251,084 B1 | * 6/2001 | Coelho | 600/585 |
| 6,589,207 B1 | * 7/2003 | El-Nounou | 604/103.04 |
| 6,733,486 B1 | * 5/2004 | Lee et al. | 604/525 |
| 6,746,423 B1 | * 6/2004 | Wantink | 604/103.04 |

* cited by examiner

*Primary Examiner*—LoAn H. Thanh
(74) *Attorney, Agent, or Firm*—Fulwider Patton Lee & Utecht LLP

(57) ABSTRACT

A catheter having an elongated shaft having at least a section which is multilayered with a first layer and a second layer secured to the first layer, and a mandrel having at least a section between the first and second layers. In one presently preferred embodiment, the mandrel is in contact with an outer surface of the first layer and with an inner surface of the second layer.

8 Claims, 2 Drawing Sheets

CATHETER HAVING A MULTILAYERED SHAFT SECTION WITH A REINFORCING MANDREL

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S Pat. No. 5,458,615 (Klemm et al.), which are incorporated herein by reference.

An essential step in effectively performing a PTCA procedure is properly positioning the balloon catheter at a desired location within the coronary artery. To properly position the balloon at the stenosed region, the catheter shaft must be able to transmit force along the length of the catheter shaft to allow it to be pushed through the vasculature. However, the catheter shaft must also retain sufficient flexibility to allow it to track over a guidewire through the often tortuous vasculature. Additionally, the catheter also must be able to cross stenosed portions of the vascular anatomy. To help meet the desire for a catheter having sufficient pushability and crossability, while maintaining trackability, prior art designs have supplemented polymer catheter shafts with a stiffening wire or mandrel. Other prior art designs have addressed these handling and performance issues by using materials of different stiffness for the proximal and distal sections of the catheter. To prevent kinking at the junction between the proximal and distal sections, while maintaining trackability and pushability, some conventional designs have employed a stiffening wire to bridge the transition in catheter shaft material. Despite these attempts, prior art designs have suffered from various drawbacks. For example, support mandrels do not always transmit axial force effectively.

Accordingly, it would be a significant advance to provide a catheter having improved pushability and crossability while maintaining good trackability. This invention satisfies these and other needs.

SUMMARY OF THE INVENTION

The invention is directed to a catheter having an elongated shaft having at least a section which is multilayered with a first layer and a second layer secured to the first layer, and a mandrel having at least a section between the first and second layers. In one presently preferred embodiment, the mandrel is in contact with an outer surface of the first layer and with an inner surface of the second layer.

In a presently preferred embodiment, the multilayered section of the shaft with the first and second layers is a proximal shaft section. In one embodiment, the first layer has a distal end located proximal to the distal end of the second layer, and the shaft has a distal shaft section comprising a distal section of the second layer extending beyond the first layer distal end. The multilayered proximal shaft section is typically about 50 to about 80% of the length of the catheter shaft. In a presently preferred embodiment, the section of the mandrel between the first and second layers is a proximal section, so that the mandrel has a proximal section secured between and in contact with the first and second layers from the proximal to the distal end of the first layer, and a distal section extending beyond the distal end of the first layer. The distal section of the mandrel extending beyond the distal end of the first layer is typically about 10 to about 40%, preferably about 20 to about 30% of the mandrel length. Alternatively, the mandrel has a distal end section located between and in contact with the first and second layers, so that in one embodiment, the entire length or at least substantially all of the length of the mandrel is located between the first and the second layers. With the reinforcing mandrel secured between the first and second layers and optionally extending beyond the end of the first layer, the catheter shaft provides improved pushability and kink resistance. Preferably, the catheter distal shaft section is relatively flexible and soft and the proximal shaft section is relatively stiff and pushable, without requiring separate longitudinal segments joined together. Thus, it should be understood that the proximal shaft section and the distal shaft section may be formed of a unitary, one piece tubular member, as for example in the embodiment in which the shaft comprises a multilayered proximal shaft section formed of the first layer secured to a surface of the second layer, and a distal shaft section formed of the portion of the second layer which extends beyond the distal end of the first layer. Consequently, the catheter of the invention has excellent pushability, trackability, and manufacturability, and preferably without external or internal junctions between longitudinal segments.

In a presently preferred embodiment, the catheter is a balloon catheter. The balloon catheter of the invention may comprise a variety of suitable balloon catheters, including coronary and peripheral dilatation catheters, stent delivery catheters, drug delivery catheters, and the like. A balloon catheter of the invention generally comprises an elongated shaft having a proximal shaft section, a distal shaft section, an inflation lumen extending within the proximal and distal shaft sections, and a guidewire receiving lumen having at least a portion extending within the distal shaft section, and an inflatable balloon on the distal shaft section with an interior in fluid communication with the inflation lumen. In a presently preferred embodiment, an inner tubular member defines the guidewire lumen, and an outer tubular member defines the inflation lumen, and the outer tubular member is the part of the shaft having at least a section which is multilayered.

In a presently preferred embodiment, the balloon catheter is an over-the-wire type catheter having a guidewire proximal port at the proximal end of the catheter shaft, a guidewire distal port at the distal end of the catheter shaft, and a guidewire lumen extending between the guidewire ports from the proximal to the distal end of the catheter shaft. In an alternative embodiment, the catheter is a rapid exchange type catheter having a guidewire proximal port in the distal shaft section spaced a relatively short distance proximally from the guidewire distal port and a relatively long distance from the proximal end of the catheter shaft, a guidewire distal port at the distal end of the catheter, and a relatively short guidewire lumen extending between the proximal and distal guidewire ports in the distal shaft section.

In a presently preferred embodiment, the reinforcing mandrel is an elongated, solid member formed of a metal such as a stainless steel. However, a variety of suitable high strength materials may be used such as a nickel-titanium (Nitinol) alloy, MP35N, and Elgiloy, and including polymeric materials such as polyetheretherketone (PEEK), polyamides, and reinforced polymers, or other suitable high strength materials from which a small diameter member can be readily formed. The mandrel typically tapers distally to a smaller outer dimension, with a gradually tapering outer diameter or one or more tapered sections intermittently located between nontapered sections. The reinforcing mandrel can have a variety of suitable transverse cross sectional shapes along all or part of the length thereof, including circular, oblong, square, and rectangular, and is typically a wire, or a ribbon with a flat transverse cross sectional shape.

The catheter of the invention is highly pushable, flexible, trackable and kink resistant due to the reinforcing mandrel secured between the first and second layers of the shaft. The shaft of the invention provides an improved transition between the proximal shaft section and the more flexible distal shaft section, for improved kink resistance. Thus, the flexible and pushable shaft provides a catheter with excellent trackability, and allows easy advancement over a guidewire and maneuvering within the patient's tortuous anatomy, to position the operative portion of the catheter at a desired location within the patient. These and other advantages of the invention will become more apparent from the following detailed description of the invention and the accompanying exemplary drawings.

DETAILED DESCRIPTION OF THE INVENTION

Figure 1:
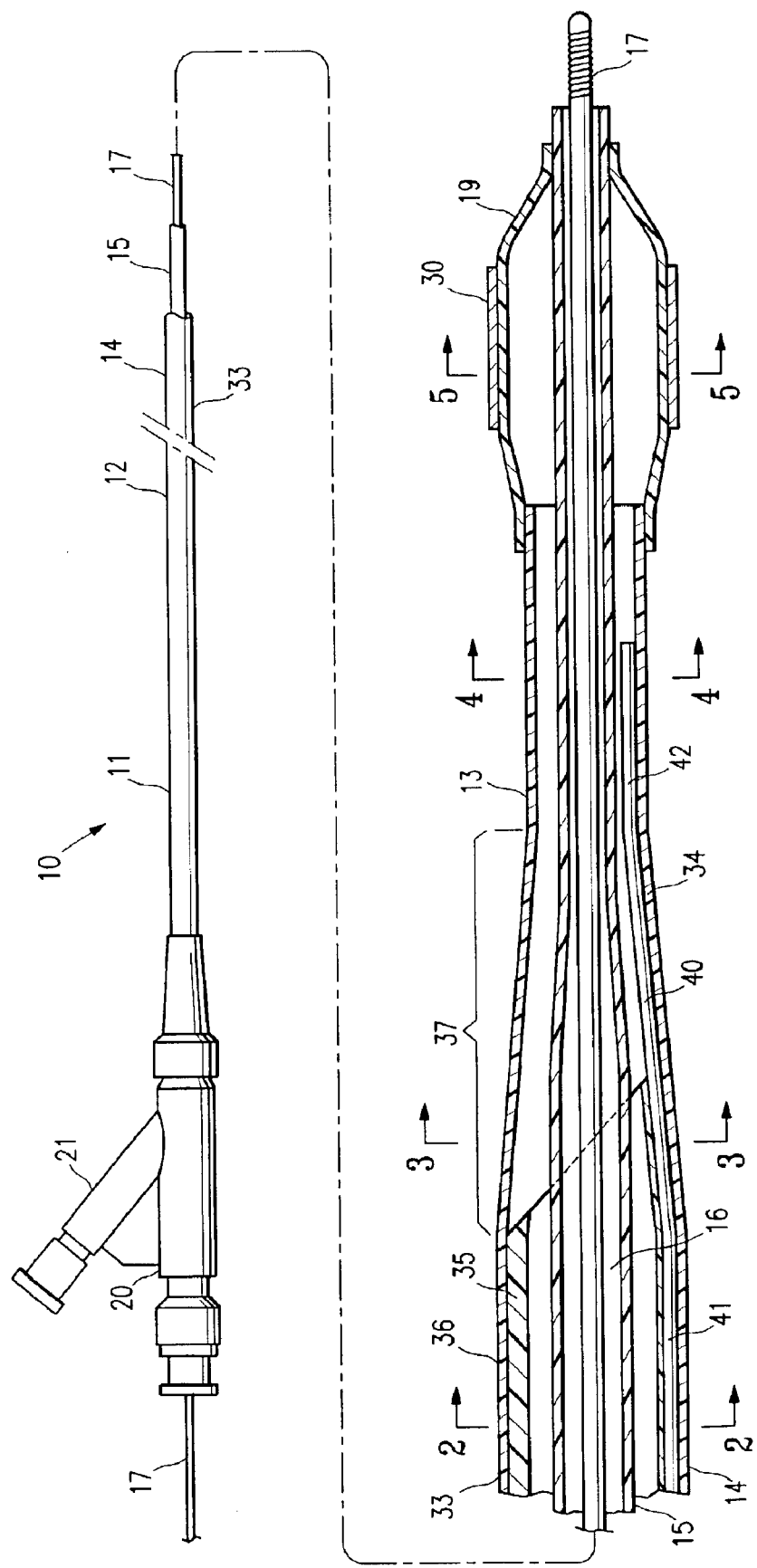
FIG. 1 is an elevational view, partially in section, of a balloon catheter which embodies features of the invention.
Figure 4:
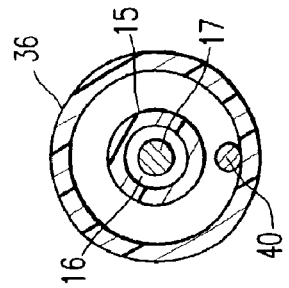
FIG. 4 is a transverse cross sectional view of the catheter shown in FIG. 1, taken along line 4—4.
Figure 7:
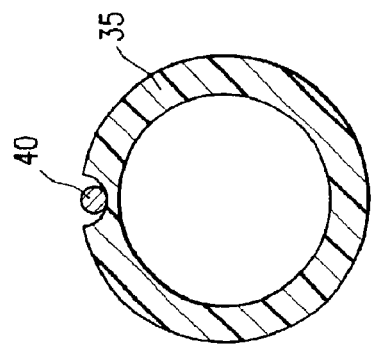
FIG. 7 is a transverse cross sectional view of the inner layer shown in FIG. 6, taken along line 7—7.
Figure 3:
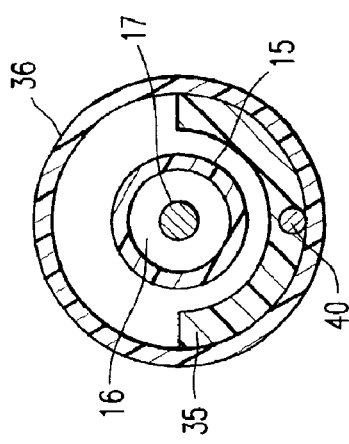
FIG. 3 is a transverse cross sectional view of the catheter shown in FIG. 1, taken along line 3—3.
Figure 2:
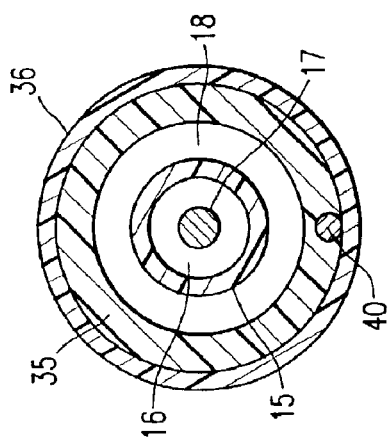
FIG. 2 is a transverse cross sectional view of the catheter shown in FIG. 1, taken along line 2—2.
Figure 5:
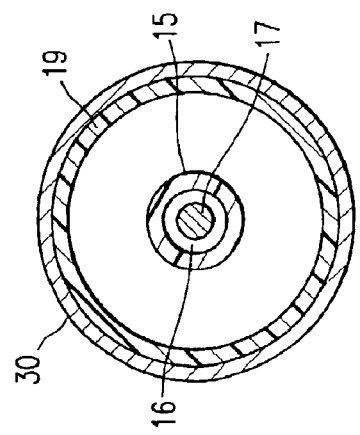
FIG. 5 is a transverse cross sectional view of the catheter shown in FIG. 1, taken along line 5—5.

FIG. 1 illustrates an over-the-wire balloon catheter 10 embodying features of the invention. Catheter 10 generally comprises an elongated catheter shaft 11 having a proximal end, a distal end, a proximal shaft section 12, a distal shaft section 13, an outer tubular member 14, and an inner tubular member 15. Inner tubular member 15 defines a guidewire lumen 16 adapted to slidingly receive a guidewire 17. The coaxial relationship between outer tubular member 14 and inner tubular member 15 defines annular inflation lumen 18, as best shown in FIGS. 2–4, illustrating transverse cross sections of the catheter of FIG. 1, taken along lines 2—2, 3—3 and 4—4, respectively. An inflatable balloon 19 is disposed on the distal shaft section 13, having a proximal skirt section sealingly secured to the distal end of outer tubular member 14, and a distal skirt section sealingly secured to the distal end of inner tubular member 15, so that its interior is in fluid communication with inflation lumen 18. An adapter 20 at the proximal end of the shaft is configured to provide access to guidewire lumen 16, and to direct inflation fluid through arm 21 into inflation lumen 18. FIG. 1 illustrates the balloon 19 prior to complete inflation, with an expandable stent 30 mounted on a working length of the balloon. The distal end of the catheter may be advanced to a desired region of a patient's body lumen in a conventional manner, and balloon 19 inflated to expand stent 30, and the balloon deflated, leaving stent 30 implanted in the body lumen. FIG. 5 illustrates a transverse cross section of the catheter of FIG. 1, taken along line 5—5.

In the embodiment illustrated in FIG. 1, the outer tubular member 14 has a multilayered proximal shaft section 33, and a distal shaft section 34. The multilayered proximal shaft section 33 of the outer tubular member 14 has a first polymeric layer 35, and a second polymeric layer 36 coaxially disposed around and secured to the first layer 35. The distal end of the first layer 35 is located proximal to the distal end of the second layer 36, so that the distal shaft section 34 of the outer tubular member 14 is formed by a distal section of the second layer 36 extending beyond the distal end of the first layer 35, i.e., a one-piece tubular member forms the outer layer 36 of the outer tubular member proximal section 33 and the entire distal section 34 of the outer tubular member 14 in the embodiment of FIG. 1. The first and second layers 35, 36 are secured together along at least a substantial length of, and typically the entire length of, the first layer 35, as for example by heat fusion bonding or adhesive bonding the layers together.

In the embodiment illustrated in FIG. 1, the distal end of the first layer 35 is truncated with a tapering wedge-like shape. The truncated distal end section of the first layer 35 is located at a tapered section 37 of the outer tubular member 14. Specifically, in the embodiment of FIG. 1, the truncated distal end of the first layer 35 has a proximal end at the proximal end of the tapered section 37 of the outer tubular member 14 and a distal end located proximal to the distal end of the tapered section 37 of the outer tubular member 14. The truncated distal end of the first layer 35, extending at an angle distally, provides an improved transition between the relatively stiff proximal section 12 and the relatively flexible distal section 13 of the shaft 11, to reduce kinking. The truncated distal end of the first layer 35 is typically about 20 cm to about 35 cm, preferably about 25 cm to about 35 cm in length. The tapered section 37 of the outer tubular member 14 typically has a length of about 4 inches to about 6 inches, along which the outer tubular member 14 tapers from an outer diameter of about 0.042 to about 0.046 inches (0.11 to 0.12 cm), to an outer diameter of about 0.031 to about 0.036 inches (0.08 to 0.09 cm).

In the embodiment of FIG. 1, the second layer 36 of the multilayered proximal section 33 (and the distal section 34) of the outer tubular member 14 is preferably formed of a polyamide such as polyether block amide (PEBAX), and more specifically PEBAX 72D (having a Shore durometer hardness of about 72D), available from Autochem. However a variety of suitable polymers may be used including nylons such as nylon 12 and L20, and including other grades of PEBAX having a Shore durometer hardness lower than that of PEBAX 72D, such as PEBAX 63D. The PEBAX tubular member forming the second layer 36 of the outer tubular member multilayered proximal section 33, and the outer tubular member distal section 34 is typically formed by extrusion and necking, resulting in a one-piece tapered PEBAX tubular member. The first layer 35 of the multilayered proximal section 33 is preferably formed of a polymeric material having a higher Shore Durometer hardness than the one-piece tapered PEBAX tubular member (i.e., the second layer 36 of the outer tubular member proximal section 33, and the outer tubular member distal section 34), to provide a relatively stiff proximal shaft section 12. The first layer 35 of the multilayered proximal section 33 of the outer tubular member 14 is preferably formed of a high strength polymer such as polyetheretherketone (PEEK), however a variety of suitable polymers may be used including polyamide, reinforced polymers. The PEEK is typically plasma treated to facilitate fusing the first layer 35 to the second layer 36. Additionally, in the embodiment of FIG. 1, the first layer 35 of the multilayered proximal section 33 has a greater wall thickness than the one-piece tapered PEBAX tubular member, to further increase the stiffness of the proximal shaft section 12 relative to the distal shaft section 13. In one embodiment, the first layer 35 of the multilayered proximal section 33 has a wall thickness of about 0.003 to about 0.004 inches (0.008 to 0.01 cm), and the second layer 36 of the multilayered proximal section 33 has a wall thickness of about 0.002 to about 0.003 inches (0.005 to 0.008 cm), and the distal section 34 of the outer tubular member 14 has a wall thickness of about 0.005 to about 0.006 inches (0.013 to 0.015 cm).

In the embodiment of the FIG. 1, a mandrel 40 has a proximal section 41 secured between and in contact with the first and second layers 35, 36 of the multilayered proximal section 33 of the outer tubular member 14, and a distal section 42 extending beyond the distal end of the first layer 35. The proximal section 41 of the mandrel 40 is in contact with an outer surface of the first layer 35 and in inner surface of the second layer 36. Thus, a portion of the first layer 35 is separated from a portion of the outer layer 36 by the mandrel 40. In an alternative embodiment (not shown), the first layer 35 of the outer tubular member multilayered proximal section 33 is on an outer surface of the second layer 36, so that the mandrel 40 is in contact with an outer surface of the second layer 36 and in inner surface of the first layer 35. The distal section 42 of the mandrel 40 is within the inflation lumen 18. In a presently preferred embodiment, the distal section 42 of the mandrel 40 is not secured to the shaft 12, and is thus free within the inflation lumen 18 between the distal section of the inner tubular member and the distal section of the outer tubular member 14, for improved flexibility and kink resistance. However, at least a portion of the distal section 42 of the mandrel 40 may alternatively be secured to the distal section 34 of the outer tubular member 14, as for example by adhesive bonding. The proximal end of the mandrel is typically secured, for example by an adhesive, to the proximal adapter 20. In the embodiment illustrated in FIG. 1, the distal end of the mandrel 40 is proximal to the proximal skirt section of the balloon 19. However, in alternative embodiments (not shown), the distal end may be located distal to the proximal skirt section of the balloon 19, for example at the radiopaque markers on the shaft or at the distal end of the balloon interior.

The mandrel 40 typically has a length of about 100 to about 143 cm, preferably about 106 to about 135 cm, depending on the length of the catheter, so that the mandrel length is typically about 70 to about 100%, preferably about 85 to about 90% of the length of the shaft 11. The mandrel 40 typically tapers distally to a smaller outer diameter. In one embodiment, the mandrel 40 has a proximal portion with a constant outer transverse dimension or diameter of about 0.015 to about 0.018 inches (0.38 to 0.46 mm), a proximal tapered portion tapering distally to a smaller outer transverse dimension of about 0.006 to about 0.009 inches (0.15 to 0.23 mm), and a distal tapered portion tapering distally to a smaller outer transverse dimension of about 0.002 to about 0.003 inches (0.05 to 0.08 mm), for a mandrel with a circular transverse shape. The mandrel 40 preferably has an outer transverse dimension which is less than the wall thickness of the first layer 35 of the outer tubular member proximal section 33, and greater than the wall thickness of the second layer 36 of the outer tubular member proximal section 33. The size of the mandrel diameter or transverse dimension relative to the wall thickness of the layers 35, 36 will depend on whether the mandrel has a circular, oblong, or other transverse shape. In one embodiment, the mandrel 40 outer transverse dimension is about 10 to about 20% less than the wall thickness of the first layer 35, and about 10 to about 20% greater than the wall thickness of the second layer 36.

The mandrel 40 is in contact with both the first layer 35 and the second layer 36 of the outer tubular member proximal section 33. The mandrel 40 is thus partially encased in the first layer 35, and a perimeter or circumference of the mandrel 40 has a first portion in contact with the first layer 35 and a second portion in contact with the second layer 36. Typically, about 75% to about 90% of the circumference of the mandrel 40 is in contact with the first layer 35, and about 10% to about 25% of the circumference of the mandrel is in contact with the second layer 36. In the embodiment illustrated in FIG. 2, about 80% to about 90% of the circumference of the mandrel 40 is in contact with the first polymeric layer 35, and about 10% to about 20% of the circumference of the mandrel is in contact with the second polymeric layer 36.

The mandrel 40 has at least a body or core which is preferably formed of stainless steel, such as L605. The stainless steel is typically full hard or spring tempered.

However, a variety of suitable materials may be used including other ferrous materials such as Nitinol, or non-ferrous materials. In the embodiment of FIG. 1, the body of the mandrel 40 is formed of a solid metal wire. The body of the mandrel 40 may be provided with a coating or outer layer along at least a section thereof. In one embodiment (not shown), the proximal section 41 of the mandrel 40 has an oblong transverse cross section, while the distal section 42 has a circular transverse cross section.

Figure 6:
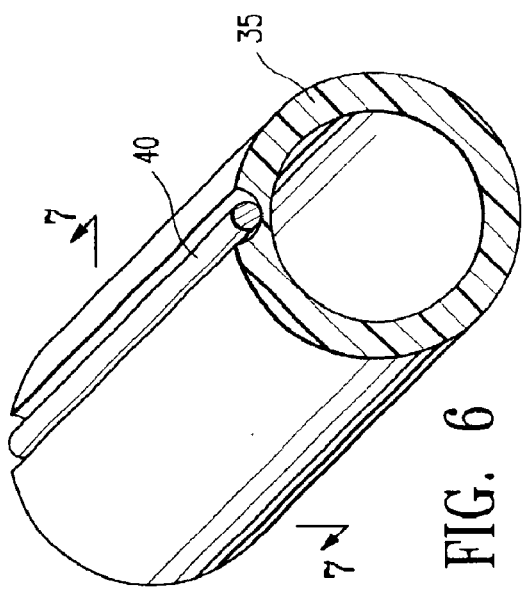
FIG. 6 is a longitudinal cross sectional view illustrating the inner layer of the outer tubular member of the catheter of FIG. 1, during manufacturing of the shaft before the outer layer is positioned on the inner layer, with the reinforcing mandrel in a groove in the inner layer.

FIG. 6 illustrates one embodiment of a polymeric tube which will form the first layer 35 of the outer tubular member proximal section 33 of the catheter of FIG. 1, during assembly of the catheter 10 before the second layer 36 is secured thereto, in one embodiment of a method of forming a catheter shaft which embodies features of the invention. In the embodiment illustrated in FIG. 6, the first layer 35 has a groove in an outer surface configured to receive the mandrel 40 therein. The groove has a semi-circular transverse cross section. The groove is preferably formed in the outer surface of the first layer 35 during extrusion of the tubular member forming the first layer 35, although it may alternatively be formed after the extrusion of the tubular member forming first layer 35, as for example by cutting or otherwise removing material from the outer surface of the first layer 35. In the embodiment illustrated in FIG. 6, the depth of the groove is about equal to the transverse dimension of the mandrel 40, so that the mandrel outer surface is aligned with (i.e., flush with) the outer surface of the first layer on either side of the groove. However, in an alternative embodiment (not shown), the groove is shallower than the mandrel so that the mandrel outer surface extends outside of the groove above the outer surface of the tube which will form the first layer 35.

During assembly of the catheter, the first layer 35, with the mandrel in the groove, is positioned in the lumen of the tubular member which forms the second layer 36. Specifically, the one-piece tubular member, which forms both the second layer 36 of the outer tubular member proximal section 33 and the outer tubular member distal section 34, is positioned around the first layer 35 (and the mandrel 40) so that the proximal section of the one-piece tubular member is surrounding the first layer 35. The second layer 36 is then secured to an outer surface of the first layer 35 as, for example, by fusing by heating during a hot air necking process with shrink tubing therearound. The shrink tubing is then removed, leaving the first and second layers 35, 36 fused together, with the proximal section 41 of the mandrel 40 secured between the first and second layers 35, 36.

To the extent not previously discussed herein, the various catheter components may be formed and joined by conventional materials and methods. For example, inner tubular member 15 can be formed by conventional techniques, such as by extruding and necking materials found useful in intravascular catheters such a polyethylene, polyvinyl chloride, polyesters, polyamides, polyimides, polyurethanes, and composite materials, and is preferably a multilayered tubular member. Additionally, although not illustrated, coiled or braided reinforcements may be included in the shaft at various locations, as is conventionally known.

The length of the dilatation catheter 10 is generally about 108 to about 200 centimeters, preferably about 137 to about 145 centimeters, and typically about 140 centimeters for PTCA. The outer tubular member 14 distal section has an outer diameter (OD) of about 0.028 to about 0.036 inch (0.70–0.91 mm), and an inner diameter (ID) of about 0.024 to about 0.035 inch (0.60–0.89 mm), and the outer tubular member 14 proximal section has an OD of about 0.017 to about 0.034 inch (0.43–0.87 mm), and an inner diameter (ID) of about 0.012 to about 0.022 inch (0.30–0.56 mm). The inner tubular member 15 has an OD of about 0.017 to about 0.026 inch (0.43–0.66 mm), and an ID of about 0.015 to about 0.018 inch (0.38–0.46 mm) depending on the diameter of the guidewire to be used with the catheter. The balloon 19 has a length of about 14 mm to about 46 mm, and an inflated working diameter of about 8 mm to about 40 mm.

While the present invention has been described herein in terms of certain preferred embodiments, those skilled in the art will recognize that modifications and improvements may be made without departing form the scope of the invention. For example, although the catheter 10 illustrated in the Figures is an over-the-wire balloon catheter, the catheter of the invention may be a variety of suitable catheters, including other balloon catheter configurations, guiding catheters, and the like. Additionally, although the mandrel 40 is illustrated as part of an outer tubular member in the Figures, the mandrel 40 could alternatively be part of a multilayered inner tubular member or other shaft configuration. While individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
    a) an elongated shaft having a proximal end, a distal end, an outer tubular member defining an inflation lumen and having at least a section which is multilayered with a first polymeric layer and a second polymeric layer secured to the first polymeric layer, and an inner tubular member extending within at least a distal section of the inflation lumen and defining a guidewire receiving lumen;
    b) a mandrel having at least a section between the first and second polymeric layers of the multilayered section of the outer tubular member; and
    c) an inflatable balloon on a distal shaft section having an interior in fluid communication with the inflation lumen.

2. The balloon catheter of claim 1 wherein the multilayered section of the outer tubular member is a proximal section of the outer tubular member.

3. The balloon catheter of claim 2 wherein the section of the mandrel between the first and second polymeric layers is a proximal section secured between the first and second polymeric layers from the proximal to the distal end of the first polymeric layer, and the mandrel has a distal section extending beyond the distal end of the first polymeric layer and within the inflation lumen of the shaft.

4. The catheter of claim 3 wherein the distal section of the mandrel is about 15 to about 25% of the mandrel length.

5. The catheter of claim 2 wherein the outer tubular member has a tapered section with a diameter tapering distally to a smaller diameter, formed at least in part by the second polymeric layer, and the distal end of the tapered section of the outer tubular member is distal to the distal end of the first polymeric layer.

6. The catheter of claim 2 wherein the balloon has a proximal skirt section secured to the distal end of the outer tubular member, and a distal skirt section secured to the inner tubular member, and the distal end of the mandrel is located proximal to the proximal skirt section of the balloon.

7. The balloon catheter of claim 2 wherein the inner tubular member extends from the proximal end of the shaft to a location distal to a distal end of the inflation lumen.

8. A balloon catheter, comprising:
 a) an elongated shaft having a proximal end, a distal end, an outer tubular member defining an inflation lumen, and an inner tubular member defining a guidewire receiving lumen and extending within the inflation lumen from the proximal end of the shaft to a location distal to the distal end of the inflation lumen, the outer tubular member having a multilayered proximal section with a first polymeric layer, and a second polymeric layer secured to the first polymeric layer, and a distal section formed of a distal portion of the second polymeric layer extending beyond a distal end of the first polymeric layer; and
 b) a mandrel having a proximal section secured between and in contact with the first and second polymeric layers of the multilayered proximal section from a proximal to the distal end of the first polymeric layer, and a distal section extending beyond the distal end of the first polymeric layer and within the inflation lumen of the shaft; and
 c) an inflatable balloon on a distal shaft section having an interior in fluid communication with the inflation lumen.

* * * * *